United States Patent [19]

Janusz et al.

[11] Patent Number: 4,898,887
[45] Date of Patent: Feb. 6, 1990

[54] COMPOUNDS AND COMPOSITIONS HAVING ANTI-INFLAMMATORY AND ANALGESIC ACTIVITY

[75] Inventors: John M. Janusz, Fairfield; Maurice E. Loomans, Cincinnati, both of Ohio; Thomas R. LaHann, Pullman, Wash.; Gerald B. Kasting, Wyoming, Ohio

[73] Assignee: The Procter & Gamble Company, Cincinnati, Ohio

[21] Appl. No.: 899,459

[22] Filed: Aug. 22, 1986

Related U.S. Application Data

[63] Continuation-in-part of Ser. No. 805,481, Dec. 4, 1985, abandoned, which is a continuation of Ser. No. 684,427, Dec. 20, 1984, abandoned.

[51] Int. Cl.$^4$ .................... A61K 31/16; C07C 103/60
[52] U.S. Cl. ..................................... 514/617; 260/404
[58] Field of Search ......................... 260/404; 514/617

[56] References Cited

U.S. PATENT DOCUMENTS

| | | | |
|---|---|---|---|
| 4,313,958 | 2/1982 | LaHann | 424/324 |
| 4,493,848 | 1/1985 | LaHann et al. | 424/324 |
| 4,599,342 | 7/1986 | LaHann | 514/617 |

OTHER PUBLICATIONS

Jansco et al, *Br. J. Pharm. Chemother.*, vol. 3, (1967), pp. 138-151.
Szolesanyi et al, *Arzneim.-Forsch.*, vol. 25, (1975), pp. 1871-1881.
Szolesanyi et al, *Arzneim-Forsch.*, vol. 26, (1976), pp. 33-37.
Yaksh et al, *Science*, vol. 260, (1979), pp. 481-483.
Virus et al, *Life Sciences*, vol. 24, (1979), pp. 1273-1281.
Arvier et al, *Br. J. Pharm.*, vol. 59, (1977), pp. 61-68.
Kiernan, *J. Exp. Physiol.*, vol. 62, (1977), pp. 151-161.

*Primary Examiner*—Charles F. Warren
*Assistant Examiner*—Carolyn S. Elmore
*Attorney, Agent, or Firm*—Milton B. Graff, IV; Kim William Zerby; Jack D. Schaeffer

[57] ABSTRACT

Trienamide and tetraenamide compounds, and pharmaceutically-acceptable salts thereof, of the formula:

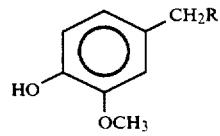

wherein R is a straight or branched chain tri-unsaturated or tetra-unsaturated fatty acid amide having from 14 to 24 carbon atoms, exhibit anit-inflammatory and analgesic activity when administered to humans or lower animals.

21 Claims, No Drawings

COMPOUNDS AND COMPOSITIONS HAVING ANTI-INFLAMMATORY AND ANALGESIC ACTIVITY

This is a continuation-in-part of application Ser. No. 805,481, filed on Dec. 4, 1985, now abandoned, which is a continuation of abandoned application Ser. No. 684,427, filed on Dec. 20, 1984, now abandoned.

TECHNICAL FIELD

The present invention relates to certain trienamides and tetraenamides, and pharmaceutical compositions containing these compounds, which exhibit anti-inflammatory and analgesic activity.

BACKGROUND OF THE INVENTION

Inflammation, or the "inflammatory response", is the result of complex interconnected physiological events, including increased vascular permeability, fluid accumulation, and the migration of a changing population of inflammaory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis-like conditions, and the like. The inflammatory response is generally believed to be a primary defense mechanism in the body, but, unchecked, can become excessive and can result in functional impairment.

The use of non-steroidal anti-inflammatory, antipyretic and analgesic drugs, especially the salicylates, which include aspirin and aspirin derivatives, to combat inflammation and attendant pain is accepted medical practice. The non-steroidals are commonly employed to relieve pain and inflammation associated with, for example, bursitis, arthritis, and the like.

While "pain" is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics merperidine, and methadone; and antipyretic analgesics, such as aspirin, phenacetin, acetaminophen, phenylbutazone, and indomethacin.

Although the precise pharmacological action of these analgesics is uncertain, there are certain effects which readily distinguish the opioid analgesics from the antipyretics. In particular, the antipyretics are weak analgesics, with much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad-based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance, as well as psychic and physical dependence.

It has been recently discovered that capsaicin, a natural product of certain species of the genus Capsicium, induces analgesia. Capsaicin (8-methyl-N-vanillyl-6-nonenamide) and "synthetic" capsaicin (N-vanillyl-nonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al., Science, 206, pp. 481–483 (1979); Jancso, et al., Naunyn-Schmiedeberg's Arch. Pharmacol., Vol. 311, pp. 285–288 (1980) and Holzer et al., Eur. J. Pharm., Vol. 58, pp. 511–514 (1979). U.S. Pat. No. 4,238,505, Nelson, issued Dec. 9, 1980, discloses 3-hydroxyacetanilide for use in producing analgesia in animals. European patent application 0089710, LaHann, et al., published Sept. 28, 1983, describes hydroxyphenylacetamides with analgesic and anti-irritant activity. Similarly, analgesic and anti-irritant activity is disclosed for N-vanillyl sulfonamides in U.S. Pat. No. 4,401,663, Buckwalter, et al., issued Aug. 30, 1983; hydroxyphenyl-acetamides in U.S. Pat. No. 4,424,205, LaHann, et al, issued Jan. 31, 1984; N-(3- or 4-hydroxy or 3,4-dihydroxybenzyl) carbamates in U.S. Pat. No. 4,443,473, Buckwalter, et al, issued Apr. 17, 1984; N-[(substituted phenyl)methyl]-cis-monounsaturated alkenamides in U.S. Pat. No. 4,493,848, LaHann, et al, issued Jan. 15, 1985; N-(3-methoxy-4-hydroxybenzyl and phenyl) ureas and thioureas in U.S. Pat. No. 4,460,602, Buckwalter, et al, issued July 17, 1984; N-vanillylureas in European patent application 0068590, Buckwalter, et al, published Jan. 5, 1983; N-[(substituted phenyl)methyl]alkynamides in U.S. Pat. No. 4,532,139, Janusz, et al, issued July 30, 1985; methylene substituted N-[(substituted phenyl)methyl]alkanamides in U.S. Pat. No. 4,544,668, Janusz, et al., issued Oct. 1, 1985; N-[(substituted phenyl)methyl]-diunsaturated amides in U.S. Pat. No. 4,544,669, LaHann, et al, issued Oct. 1, 1985; monoalkenamides in U.S. Pat. No. 4,564,633, LaHann, et al, issued Jan. 14, 1986; substituted phenylacetic acid esters in British Patent Specification No. 2,168,974, Loomans, et al, published July 2, 1986; N-(substituted alkyl)alkanamides and thioamides in British Patent Specification No. 2,168,976, Loomans, et al, published July 2, 1986; substituted aromatic-araalkanamides in British Patent Specification No. 2,168,975, Janusz et al, published July 2, 1986; combinations of capsaicinoids and arylalkanoic acids in U.S. patent application No. 684,642, Brand, filed Dec. 24, 1984 and in European patent application publication No. 149,545, Brand, published July 24, 1985; and combinations of capsaicinoids and opioids in U.S. Pat. No. 4,599,342, LaHann, issued July 8, 1986.

It has now been discovered that certain trienamides and tetraenamides have anti-inflammatory and analgesic activity in humans and lower animals. Some of these compounds have analgesic potency far greater than that of aspirin and comparable to that of the opioids, but do not exhibit undesirable narcotic side effects such as tolerance and physical dependence. These compounds are also less toxic than capsaicin.

SUMMARY OF THE INVENTION

The present invention provides compounds useful for reducing inflammation and producing analgesia in humans and lower animals, which compounds have the formula:

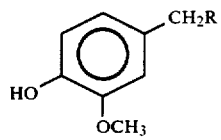

wherein R is straight or branched chain tri-unsaturated or tetra-unsaturated fatty acid amide having from 14 to 24 carbon atoms; and pharmaceutically-acceptable salts thereof.

This invention also provides pharmaceutical compositions comprising a safe and effective amount of these compounds, or mixtures thereof, and a pharmaceutically-acceptable carrier. Also provided are methods for producing analgesia and reducing inflammation by administering the compounds and compositions of this invention.

DESCRIPTION OF THE INVENTION

The compositions and methods of this invention incorporate certain N-vanillyl trienamides or N-vanillyl tetraenamides, or pharmaceutically-acceptable salts thereof, of the formula:

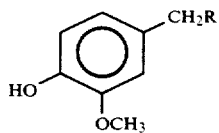

wherein R is a straight or branched chain tri-unsaturated or tetra-unsaturated fatty acid amide (preferably a cis, straight-chain triunsaturated fatty acid amide) having from 14 to 24 carbon atoms, and preferably from 18 to 20 carbon atoms.

Preferred trienamides include those wherein R is derived from such cis-triunsaturated fatty acids as 11Z,14Z,17Z-eicosatrienoic acid, γ-linolenic acid, and linolenic acid. Preferred tetraenamides include those wherein R is derived from such cis-tetraunsaturated fatty acids as arachidonic acid, and thus the particularly preferred tetraenamide of the present invention is N-vanillyl-5Z,8Z,11Z,14Z-eicosatetraenamide (i.e., N-vanillylarachidonamide). Particularly preferred trienamides include N-vanillyl-9Z,12Z,15Z-octadecatrienamide (N-vanillyl-linolenamide), N-vanillyl-6Z,9Z,12Z-octadecatrienamide (N-vanillyl-γ-linolenamide), and N-vanillyl-11Z,14Z,17Z-eicosatrienamide. The most preferred trienamide for anti-inflammatory activity is N-vanillyl-6Z,9Z,12Z-octadecatrienamide. The most preferred trienamide for analgesic activity is N-vanillyl-11Z,14Z,17Z-eicosatrienamide, which appears to have analgesic activity comparable to that of the opioids, but does not exhibit undesirable narcotic side effects. Preferred pharmaceutically-acceptable trienamide and tetraenamide salts include the sodium, potassium, calcium, magnesium, and ammonium salts.

The trienamides and tetraenamides described herein can be readily prepared by the following general synthetic scheme:

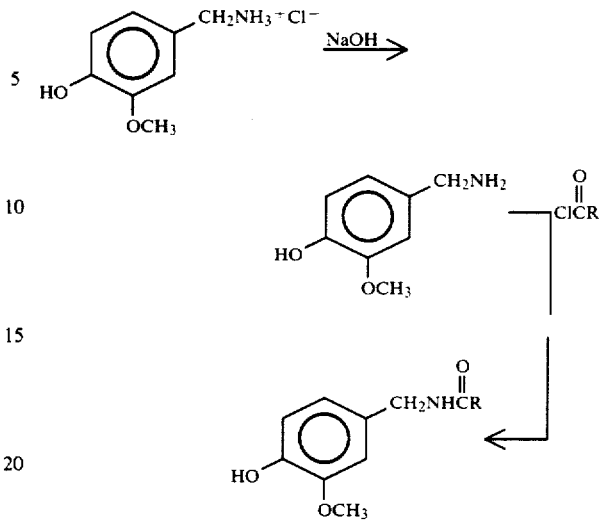

The fatty acids used in the synthesis of preferred trienamides and tetraenamides are commercially-available.

COMPOSITIONS

The compositions of the present invention comprise:
(a) a safe and effective amount of a trienamide or tetraenamide as defined herein; and
(b) a pharmaceutically-acceptable carrier.

A safe and effective amount of trienamide or tetraenamide is that amount which provides anti-inflammatory activity and analgesia, thereby alleviating or preventing the inflammation or pain being treated at a reasonable benefit/risk ratio, as is intended with any medical treatment. Obviously, the amount of trienamide or tetraenamide used will vary with such factors as the particular condition that is being treated, the severity of the condition, the duration of the treatment, the physical condition of the patient, the nature of concurrent therapy (if any), the route of administration, the specific formulation and carrier employed, and the solubility and concentration of trienamide or tetraenamide therein.

Depending upon the particular route of administration, and compatibility with the active chosen, a variety of pharmaceutically-acceptable carriers, well-known in the art, may be used. These include solid or liquid filler, diluents, hydrotropes, excipients, surface-active agents, and encapsulating substances. The amount of the carrier employed in conjunction with the trienamide or tetraenamide is sufficient to provide a practical quantity of material per unit dose.

Pharmaceutically-acceptable carriers for systemic administration that may be incorporated into the compositions of this invention, include sugars, starches, cellulose and its derivatives, malt, gelatin, talc, calcium sulfate, vegetable oil, synthetic oils, polyols, alginic acid, phosphate buffer solutions, emulsifiers, isotonic saline, and pyrogen-free water. Specific pharmaceutically-acceptable carriers are described in the following U.S. patents and European patent applications, all incorporated by reference herein: U.S. Pat. No. 4,401,663, Buckwalter, et al., issued Aug. 30, 1983; European patent application 0089710, LaHann, et al., published Sept. 28, 1983; and European patent application 0068592, Buckwalter, et al., published Jan. 5, 1983.

Preferred carriers for parenteral administration include propylene glycol, ethyl oleate, pyrrolidone, ethanol, and vegatable oils. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50% of the amide of the present invention. Tablets can be compressed, tablet triturates, enteric-coated, sugar-coated, film-coated or multiple compressed, containing suitable binders, lubricants, diluents, disintegrating agents, coloring agents, flavoring agents, preservatives, flow-inducing agents, and melting agents. Liquid oral dosage forms include aqueous solutions, emulsions, suspensions, solutions and/or suspensions reconstituted from noneffervescent granules and effervescent preparations reconstituted from effervescent granules, containing suitable solvents, preservatives, emulsifying agents, suspending agents, diluents, sweeteners, melting agents, coloring agents, and flavoring agents. Preferred carriers for oral administration include gelatin, propylene glycol, ethyl oleate, cottonseed oil and sesame oil. Specific examples of pharmaceutically-acceptable carriers and excipients that may be used to formulate oral dosage forms, which may be used in formulating oral dosage forms containing the amides of the present invention, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*, Vol. 7 (Banker and Rhodes, editors), 359–427 (1979), incorporated by reference herein.

The compositions of the present invention can also be administered topically to a biologic subject, i.e., by the direct laying on or spreading of the composition on epidermal or epithelial tissue. Such compositions include lotions, creams, solutions, gels and solids. These topical compositions comprise a safe and effective amount, usually at least about 0.5%, and preferably from about 1% to about 5%, of the amide of the present invention. Suitable carriers for topical administration of the amide preferably remain in place on the skin as a continuous film and resist being washed off easily by perspiration or by immersion in water. Generally, the carrier is either organic in nature or an aqueous emulsion and capable of having the amide dispersed or dissolved therein. The carrier may include pharmaceutically-acceptable emollients, coloring agents, fragrances, emulsifiers, thickening agents, and solvents.

Specific systemic and topical formulations useful in this invention are described in the following U.S. patents and European patent applications, all incorporated by reference herein: U.S. Pat. No. 4,401,663, Buckwalter, et al., issued Aug. 30, 1983; and European patent application 0089710, LaHann, et al., published Sept. 28, 1983; European patent application No. 0068590, Buckwalter, et al., published Jan. 5, 1983; and European patent application 0068592, Buckwalter, et al., published Jan. 5, 1983. Topical vehicles, useful herein, are disclosed in the following U.S. patents, incorporated by reference herein: "Penetrating Topical Pharmaceutical Compositions Containing 1-dodecyl-azacycloheptan-2-one", U.S. Pat. No. 4,557,934, Cooper, issued Dec. 10, 1985; and "Penetrating Topical Pharmaceutical Compositions Containing N-(2-hydroxyethyl)-pyrrolidone", U.S. Pat. No. 4,537,776, Cooper, issued August 27, 1985. Additional formulations, useful for parenteral, oral, and topical administration of amides of the present invention, are disclosed in the following U.S. patents all incorporated by reference herein: "Compositions and Methods Useful for Producing Analgesia", U.S. Pat. No. 4,493,848, LaHann and Buckwalter, issued Jan. 15, 1985; "Compounds and Compositions Useful for Producing Analgesia", U.S. Pat. No. 4,544,669, LaHann, Janusz, and Buckwalter, issued Oct. 1, 1985; "Compounds and Compositions Useful for Producing Analgesia", U.S. Pat. No. 4,532,139, Janusz and LaHann, issued July 30, 1985; and "Compounds and Compositions Useful for Producing Analgesia", U.S. Pat. No. 4,544,668, Janusz, Buckwalter and LaHann, issued Oct. 1, 1985.

METHODS FOR PRODUCING ANTI-INFLAMMATORY ACTIVITY AND ANALGESIA

The present invention also encompasses methods of producing anti-inflammatory activity and analgesia in humans or lower animals through adminstering, to the human or lower animal, a safe and effective amount, usually from about 1 mg to about 3600 mg per day, preferably from about 200 mg to about 2000 mg per day, of an amide compound described herein. While dosages higher than the foregoing are effective to reduce inflammation and produce analgesia, care must be taken in some individuals to prevent adverse side effects. The compounds and compositions of this invention can be used to treat and prevent pain, to provide analgesia, and to reduce inflammation in various disorders at the deeper structures, muscles, tendons, bursa and joints associated with disease and trauma, and in various other conditions in which non-steroidal anti-inflammatory, antipyretic and analgesic drugs such as aspirin and opioids such as morphine have heretofore been used to alleviate pain and discomfort and reduce inflammation.

The compounds and compositions of the instant invention can be administered topically or systemically. Systemic application includes any method of introducing the amide compound into the tissues of the body, e.g., intrathecal, epidural, intramuscular, transdermal, intravenous, intraperitoneal, subcutaneous, sublingual, and oral administration.

A preferred method of parenteral administration is through intramuscular injection. As is known and practiced in the art, all formulations for parenteral administration must be sterile. For mammals, especially humans, individual doses of from about 0.025 mg/kg to about 6.0 mg/kg of the amide of the present invention are acceptable. Thus, a human weighing approximately 70 kg could be given an individual dose of from about 2 mg to about 400 mg of the amide. Individual doses of from about 1.0 mg/kg to about 3.0 mg/kg are preferred. Although frequency of administration will be determined by the duration of activity of the particular amide administered, which is variable, the amides are generally long-acting, and in some cases it may be possible to obtain effective relief by administering the composition as infrequently as once every 2–3 days.

A preferred method of systemic application of the amides is through oral administration. For mammals, especially humans, individual doses of from about 0.015 mg/kg to about 20 mg/kg of the amide are acceptable. Thus, a human weighing approximately 70 kg could be given an individual dose of from about 1 mg to about 1500 mg of the amide. Individual doses of from about 1.0 mg/kg to about 8.0 mg/kg are especially preferred.

Topical administration can be used to reduce inflammation and produce local or systemic analgesia, through directly laying on or spreading a safe and effective amount of the amide of the present invention, or composition containing an amide of the present invention, on epidermal or epithelial tissue, including outer skin and oral, gingival, and nasal tissue. The amount of the pharmaceutical composition to be topically administered may vary from about 1 mg/cm² to 5 mg/cm², and if a patch is worn over the affected area possibly higher, depending upon such factors as the sensitivity, type and location of tissue to be treated, the composition and carrier (if any) to be administered, and the particular amide to be administered as well as the particular disorder to be treated and the extent to which systemic (as distinguished from local) effects are desired. The extent of systemic analgesia also depends upon such factors as the amount of the amide, the area of tissue to be covered, and the ability of the amide composition to penetrate the skin tissues.

The following non-limiting Examples illustrate the compounds, compositions, and methods of treatment of the present invention.

EXAMPLE I

N-vanillyl-6Z,9Z,12Z-octadecatrienamide was synthesized by the following method:

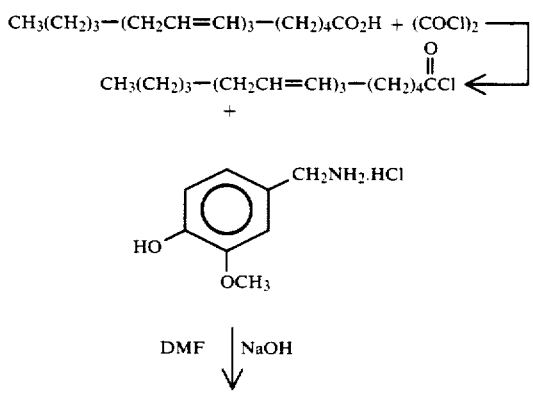

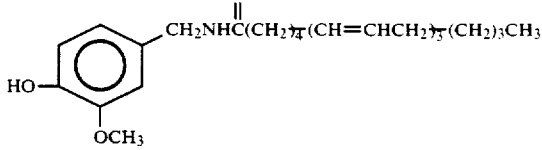

Specifically, 3.17 g (2.18 ml) of oxalyl chloride and 5 g of γ-linolenic acid were added to 30 ml of dry methylene chloride, and the mixture was refluxed for approximately 90 minutes, until gas evolution ceased. Excess oxalyl chloride and the solvent were evaporated. 3.41 g of vanillylamine hydrochloride was suspended in 60 ml of N,N-dimethylformamide (DMF). 7.2 ml of 5N NaOH was added, and the mixture was stirred at room temperature for 10 minutes, then cooled to 0° C. 40 ml of ether was added to the γ-linolenic acid chloride, and the resulting solution was added dropwise to the vanillylamine mixture over a 20 minute time period. The mixture was allowed to warm to room temperature and stored overnight. The next morning, the mixture was poured into 600 ml of water, and extracted with 250 ml of ether. This process was repeated 3 times. Extracts were combined and washed with 1N HCl, saturated NaHCO₃, and brine, dried over MgSO₄, and evaporated. 7.2 g of crude N-vanillyl-6Z,9Z,12Z-octadecatrienamide was obtained. The crude product was flash chromatographed with 33% EtOAC/hexane. 5.45 g of analytically pure product was obtained.

In the above example, N-vanillyl-9Z,12Z,15Z-octadecatrienamide was made by substituting the appropriate linolenic acid in the above synthesis. Also in the above example, N-vanillyl-5Z,8Z,11Z,14Z-eicosatetraenamide is made by essentially the same method by substituting arachidonic acid in the above synthesis.

EXAMPLE II

N-vanillyl-11Z,14Z,17Z-eicosatrienamide was synthesized by the following method:

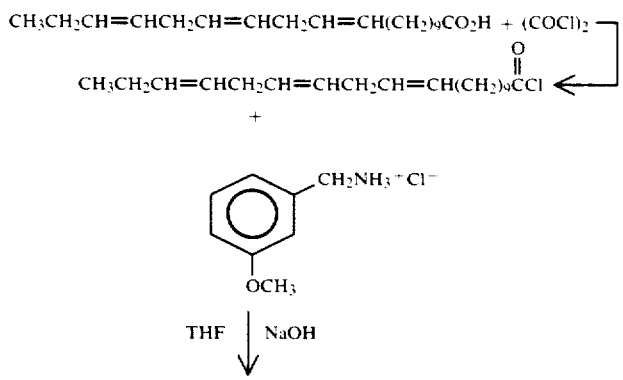

-continued

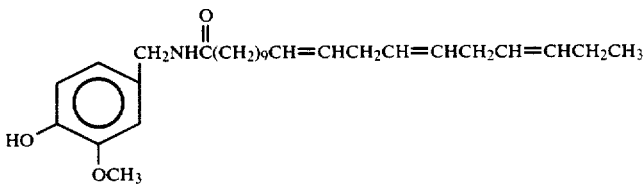

Specifically, 1.2 ml of oxalyl chloride was added to 4.0 g of eicosatrienoic acid in 10 ml of chloroform and stirred at room temperature for 60 minutes, then warmed to 50° C. for 20 minutes. Excess solvent and oxalyl chloride were evaporated. 5.76 ml of 5N NaOH was then added to 2.71 g of vanillylamine hydrochloride in 50 ml of tetrahydrofuran (THF) and stirred for 15 minutes. 25 ml of ether was added to the acid chloride and the resulting solution was added dropwise to the vanillylamine mixture over 15 minutes. The reaction was stirred at room temperature and then refrigerated overnight. The following morning, the solvent was evaporated and the residue partitioned between 50 ml ethyl ether and 50 ml water. The organic phase extract was washed with 1N HCl, saturated $NaHCO_3$, $H_2O$, and brine, and then dried over $MgSO_4$, filtered, and evaporated. 6.0 g crude N-vanillyl-11Z,14Z,17Z-eicosatrienamide was obtained. The crude product was flash chromatographed with 40% EtOAc/hexane. 5.0 g of analytically pure product was obtained.

EXAMPLE III

A composition for parenternal administration is prepared by combining the following ingredients:

| | |
|---|---|
| N—vanillyl-9Z, 12Z, 15Z-octadecatrienamide | 300 g |
| Ethyl oleate | 980 ml |
| Benzyl alcohol | 20 ml |

The octadecatrienamide is dissolved in the solution combining ethyl oleate and benzyl alcohol, sealed into airtight 5 ml ampoules, and sterilized by autoclaving. Injection of 1.5 ml of the contents of one of these ampoules intramuscularly into a 65 kg human produces analgesia and reduces inflammation.

A substantially similar reduction of inflammation, and a similar analgesic effect, is obtained when N-vanillyl-9Z,12Z,15Z-octadecatrienamide is replaced with N-vanillyl-6Z,9Z,12Z-octadecatrienamide, or N-vanillyl-11Z,14Z,17Z-eicosatrienamide.

A composition for parenteral administration of N-vanillyl-5Z,8Z,11Z,14Z-eicosatetraenamide is prepared by a substantially similar method. Injection of this composition intramuscualrly into a human produces analgesia and reduces inflammation.

EXAMPLE IV

A composition for oral administration is prepared by combining the following ingredients:

| | |
|---|---|
| N—vanillyl-9Z, 12Z, 15Z-octadecatrienamide | 1.10 kg |
| Sesame oil | 3.25 liters |

The octadecatrienamide is dissolved in the sesame oil with the aid of sonication and is packaged in soft gelatin capsules using methods known in the art. Two of the resulting capsules, each containing 225 mg of the composition, are administered to a 60 kg human, producing analgesia and reducing inflammation.

A substantially similar reduction of inflammation, and a similar analgesic effect, is obtained when the N-vanillyl-9Z,12Z,15Z-octadecatrienamide is replaced with N-vanillyl-6Z,9Z,12Z-octadecatrienamide, or N-vanillyl-11Z,14Z,17Z-eicosatrienamide.

A composition for oral administration of N-vanillyl-5Z,8Z,11Z,14Z-eicosatetraenamide is prepared by a substantially similar method. Oral administration of this composition to a human produces analgesia and reduces inflammation.

EXAMPLE V

A composition for oral administration is prepared by combining the following ingredients:

| | |
|---|---|
| N—vanillyl-9Z, 12Z, 15Z-octadecatrienamide | 250 g |
| Propylene glycol | 1800 ml |
| Ethyl alcohol | 175 ml |
| Distilled water | 75 ml |
| Artificial Strawberry flavor | 10 ml |
| FD&C Red #40 | 0.2 g |

The above ingredients are combined to produce a syrup and are packaged under sterile conditions in 6 oz. bottles. One teaspoon of this formulation is administered to a 70 kg adult human, reducing inflammation and producing analgesia.

A substantially similar reduction of inflammation, and a similar analgesic effect, is obtained when the N-vanillyl-9Z,12Z,15Z-octadecatrienamide is replaced with N-vanillyl-6Z,9Z,12Z-octadecatrienamide, or N-vanillyl-11Z,14Z,17Z-eicosatrienamide.

A composition for oral administration of N-vanillyl-5Z,8Z,11Z,14Z-eicosatetraenamide is prepared by a substantially similar method. Oral administration of this composition to a human produces analgesia and reduces inflammation.

EXAMPLE VI

A composition for topical administration is prepared by combining the following ingredients:

| | |
|---|---|
| N—vanillyl-9Z, 12Z, 15Z-octadecatrienamide | 4 g |
| Propylene glycol | 100 ml |
| Ethyl alcohol | 100 ml |

The octadecatrienamide is melted to a liquid with slight warming and combined with the other ingredients. Application of 0.4 ml of the resulting liquid to a 80 $cm^2$ portion of the forearm of a 60 kg human reduces inflammation and produces analgesia.

A substantially similar reduction of inflammation, and a similar analgesic effect, is obtained with the N-vanillyl-9Z,12Z,15Z-octadecatrienamide is replaced with N-vanillyl-6Z,9Z,12Z-octadecatrienamide or N-vanillyl-11Z,14Z,17Z-eicosatrienamide.

A composition for topical application of N-vanillyl-5Z,8Z,11Z,14Z-eicosatetraenamide is prepared by a substantially similar method. Topical apllication of this composition to a human produces analgesia and reduces inflammation.

Effectiveness in Reducing Inflammation and Providing Analgesia

EXAMPLE VII

Two trienamide compositions were tested for anti-inflammatory activity using the croton oil-induced mouse ear inflammation test.

Adult male Cox ICR mice, 20–30 g, were treated on the left ear at 20–28 hours prior to sacrifice and a second time 5–6 hours prior to sacrifice with 25 µl of a 1% ethanolic solution of the test compound. Four hours prior to sacrifice both ears were treated with 25 µl of a 2% solution of croton oil in acetone. Each animal was then placed in individual cages and given food and water ad lib. Animals were sacrificed by cervical dislocation and both ears removed. From these ears, 0.38 cm$^2$ punch biopsies were taken from the central portion and each biopsy weighed on a Cahn electrobalance.

For each test substance, a group of 10 animals was used. Control groups either had both ears treated with croton oil or just the right ear. It was experimentally determined that a value of 11.0 mg could be assumed for a punch biopsy from a normal untreated ear and still be within the experimental error of the test. Therefore, for the calculation of percent inhibition, a value of 11.0 mg was used.

$$\frac{\text{Weight Right Ear} - \text{Weight Left Ear}}{\text{Weight Right Ear} - \text{Weight Control Ear (11.0 mg)}} \times 100$$

This calculation is valid only when no systemic effects are noted as evidenced by comparison of right ears of treated and control groups.

Statistical signifance at the 95% confidence level was determined by the paired test.

| Compound | % Inhibition |
|---|---|
| N—vanillyl-9Z, 12Z, 15Z-octadecatrienamide | 78.5 ± 31.9 |
| N—vanillyl-6Z, 9Z, 12Z-octadecatrienamide | 100.7 ± 11.9 |

These results show that the trienamide compositions tested do in fact have statistically significant anti-inflammatory activity.

EXAMPLE VIII

Three trienamide composition were tested for analgesic and anti-inflammatory activity using the phenylquinone writhing assay.

Groups of eight male mice weighing between approximately 25 and 30 g were dosed orally by gavage with the composition to be tested. Identical groups of mice were dosed with control compositions. Three hours after this initial administration, the mice were injected intraperitoneally with a 0.2% solution of phenylbenzoquinone in aqueous ethanol. The ability of the analgesic compositions tested to relieve the discomfort induced was measured by counting the number of abdominal contractions, or "writhes", occurring in each mouse during a 10 minute period beginning 10 minutes after injection of the phenylbenzoquinone solution.

| Compound | Writhes/10 minutes |
|---|---|
| N—vanillyl-9Z, 12Z, 15Z-octadecatrienamide | 0.4 ± 0.3 |
| N—vanillyl-6Z, 9Z, 12Z-octadecatrienamide | 0.0 ± 0.0 |
| N—vanillyl-11Z, 14Z, 17Z-eicosatrienamide | 0.4 ± 0.3 |
| Vehicle Control | 17.4 ± 1.7 |

These results show that the trienamide compositions tested exhibit analgesic/anti-inflammatory activity.

Rodent Hot Plate Test

The degree of thermal analgesia obtained was determined using the "rodent hot plate test" (RHP). The RHP system is designed to detect and evaluate agents which elevate the threshold for the perception of pain. Classically, this method has been utilized primarily to evaluate opioid (narcotic) analgesic agents, such as morphine. Unless administered in toxic quantities, antipyretic analgesics, such as aspirin or acetaminophen, exhibit little or no activity in the RHP system.

Groups of 10 male CF-1 mice or 8–10 male Sprague-Dawley rats were used to evaluate each composition. The test procedure consisted of placing a particular rodent on a surface heated to 55° C. and observing its behavior. The point in time at which the rodent either rapidly fanned one of its rear paws or licked any one of its paws was noted, and the total elapsed time from the first contact with the heated surface was determined ("response time"). If the response time for a particular rodent reached sixty seconds, the rodent was removed from the hot plate so as to prevent organic damage, and the response time recorded as sixty seconds. Hence, the maximum measurable response time for any particular composition was sixty seconds.

EXAMPLE IX

An analgesic composition for oral administration was made with the following ingredients:

| | |
|---|---|
| N—vanillyllinolenamide (VL) | 400 mg |
| Propylene glycol | 5 ml |

The n-vanillyllinolenamide was dissolved in the propylene glycol with the aid of sonication. Groups of 10 male Sprague-Dawley rats (100–250 g) were dosed orally by gavage with either the vehicle (VC) alone or the analgesic composition (VL).

The analgesic activity was then measured using the Rodent Hot Plate Test described above. Rodents were considered analgesic if their post-dose latency time was greater than the sum of their individual pre-dose latency time plus 3 times the standard deviation of the group's pre-dose latency times. The percent of rodents demonstrating analgesia was measured at 1, 2, and 3 hours post-dose.

| | % Animals Analgesic | | | |
|---|---|---|---|---|
| Treatment | 1 hr. | 2 hrs. | 3 hrs. | post-dose |
| | Experiment A | | | |
| VL-200 mg/kg | 80 | 40 | | 30 |
| VC-2.5 ml/kg | 20 | 10 | | 0 |

| | Experiment B | | |
|---|---|---|---|
| VL-200 mg/kg | 50 | 60 | 20 |
| VC-2.5 ml/kg | 0 | 20 | 0 |
| | Experiment C | | |
| VL-288 mg/kg | 50 | 10 | 0 |
| VC-3.6 ml/kg | 10 | 0 | 0 |

EXAMPLE X

An analgesic composition for oral administration was made with the following ingredients:

| N—vanillyllinolenamide | 400 mg |
|---|---|
| Sesame oil | 5 ml |

The N-vanillyllinolenamide (VL) was dissolved in the sesame oil with the aid of sonication. Groups of 10 male Sprague-Dawley rats (100–250 g) were dosed orally by gavage with either the vehicle alone (VC) or the analgesic composition (VL).

The analgesic activity was then measured using the Rodent Hot Plate Test described above. The percent of rodents demonstrating analgesia was measured at 1, 2, and 3 hours post-dose.

| Treatment | % Animals Analgesic | | |
|---|---|---|---|
| | 1 hr. | 2 hrs. | 3 hrs. post-dose |
| VL-20 mg/kg | 70 | 30 | 10 |
| VC-2.5 ml/kg | 0 | 20 | 0 |

EXAMPLE XI

Analgesic compositions for oral administration at various dose levels are made as follows:

| | Composition # | | |
|---|---|---|---|
| | VA-1 | VA-2 | VA-3 |
| N—vanillyl-arachidonamide | 150 mg | 300 mg | 600 mg |
| Sesame oil | 10 ml | 10 ml | 10 ml |

The N-vanillyl-arachidonamide (VA) is dissolved in the sesame oil with the aid of sonication. Groups of 8 male Sprague-Dawley rats (100–250 g) are dosed orally by gavage with either the vehicle alone (VC) or the analgesic composition (i.e., VA-1, VA-2 or VA-3).

The analgesic activity is then measured using the Rodent Hot Plate Test described hereinbefore, except that the end point is only the hind paw licking. The percent of rodents demonstrating analgesia is measured at 1.5, 3, and 5 hours post-dose.

| Treatment | | % Animals Analgesic | | |
|---|---|---|---|---|
| Composition | Dose (mg/kg P.O.) | 1.5 hrs. | 3 hrs. | 5 hrs.post-dose |
| VC | 0 | 0 | 12 | 0 |
| VA-1 | 75 | 12 | 0 | 12 |
| VA-2 | 150 | 12 | 38 | 38 |
| VA-3 | 300 | 38 | 88 | 38 |

What is claimed is:

1. N-vanillylamide compounds, and pharmaceutically-acceptable salts thereof, of the formula:

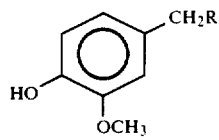

wherein R is a straight or branched chain tri-unsaturated or tetra-unsaturated fatty acid amide having from 14 to 24 carbon atoms.

2. N-vanillylamide compounds, and pharmaceutically-acceptable salts thereof, according to claim 1, wherein R is a straight or branched chain tri-unsaturated or tetra-unsaturated fatty acid amide having from 18 to 20 carbon atoms.

3. N-vanillylamide compounds, and pharmaceutically-acceptable salts thereof, according to claim 1, wherein R is a straight chain tri-unsaturated or tetra-unsaturated fatty acid amide.

4. N-vanillylamide compounds, and pharmaceutically-acceptable salts thereof, according to claim 3, wherein R is a straight chain tri-unsaturated or tetra-unsaturated fatty acid amide having from 18 to 20 carbon atoms.

5. A trienamide compound, according to claim 4, wherein said trienamide is selected from the group consisting of N-vanillyl-9Z,12Z,15Z-octadecatrienamide; N-vanillyl-6Z,9Z,12Z-octadecatrienamide; N-vanillyl-11Z,14Z,17Z-eicosatrienamide; pharmaceutically-acceptable salts thereof; and mixtures thereof of these trienamides.

6. A tetraenamide compound, according to claim 4, wherein said tetraenamide is N-vanillyl-5Z,8Z,11Z,14Z-eicosatetraenamide, and pharmaceutically-acceptable salts thereof.

7. A composition for reducing inflammation and producing analgesia in humans or lower animals comprising:

(a) a safe and effective amount of a N-vanillylamide compound of the formula

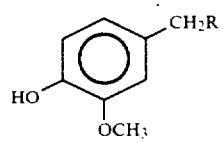

wherein R is a straight or branched chain tri-unsaturated or tetra-unsaturated fatty acid amide having from 14 to 24 carbon atoms, or a pharmaceutically-acceptable salt thereof, or mixtures thereof; and (b) a pharmaceutically-acceptable carrier.

8. A composition, according to claim 7, wherein R is a straight or branched chain tri-unsaturated or tetra-unsaturated fatty acid amide having from 18 to 20 carbon atoms.

9. A composition, according to claim 7, wherein R is a straight chain tri-unsaturated or tetra-unsaturated fatty acid amide.

10. A composition, according to claim 9, wherein R is a straight chain tri-unsaturated or tetra-unsaturated fatty acid amide having from 18 to 20 carbon atoms.

11. A composition, according to claim 10, wherein said N-vanillylamide compound is N-vanillyl-9Z,12Z,15Z-octadecatrienamide; N-vanillyl- 6Z,9Z,12Z-octadecatrienamide; or N-vanillyl-11Z,14Z,17Z-eicosatrienamide.

12. A composition, according to claim 10, wherein said N-vanillylamide compound is N-vanillyl-5Z,8Z,11Z,14Z-eicosatetraenamide.

13. A composition, according to claim 7, for parenteral administration, comprising at least about 90%, by weight, of said pharmaceutically-acceptable carrier.

14. A composition, according to claim 7, for oral administration, comprising from about 25% to about 50%, by weight, of said N-vanillylamide.

15. A composition, according to claim 7, for topical administration, comprising from about 1% to about 5%, by weight, of said N-vanillylamide.

16. A method for reducing inflammation and producing analgesia in humans or lower animals, which comprises administering to said human or lower animal a safe and effective amount of a composition comprising:
(a) a safe and effective amount of a N-vanillylamide compound of the formula

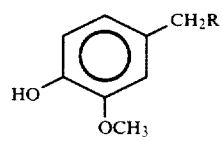

wherein R is a straight or branched chain tri-unsaturated or tetra-unsaturated fatty acid amide having from 14 to 24 carbon atoms, or a pharmaceutically-acceptable salt thereof, or mixtures thereof; and
(b) a pharmaceutically-acceptable carrier.

17. A method, according to claim 16, wherein R is a straight or branched chain tri-unsaturated or tetra-unsaturated fatty acid amide having from 18 to 20 carbon atoms.

18. A method, according to claim 17, wherein R is a straight chain tri-unsaturated or tetra-unsaturated fatty acid amide having from 18 to 20 carbon atoms.

19. A method, according to claim 18, wherein said composition is administered intramuscularly.

20. A method, according to claim 18, wherein said composition is administered orally.

21. A method, according to claim 18, wherein said composition is administered topically.

* * * * *